(12) United States Patent
Takahashi (10) Patent No.: US 12,343,178 B2
(45) Date of Patent: Jul. 1, 2025

(54) BIOLOGICAL INFORMATION DETECTION SYSTEM, WEARABLE BIOLOGICAL INFORMATION DETECTION DEVICE, AND BIOLOGICAL INFORMATION DETECTION METHOD

(71) Applicant: SEIKO EPSON CORPORATION, Tokyo (JP)

(72) Inventor: Yusuke Takahashi, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 366 days.

(21) Appl. No.: 17/680,224

(22) Filed: Feb. 24, 2022

(65) Prior Publication Data

US 2022/0273248 A1   Sep. 1, 2022

(30) Foreign Application Priority Data

Feb. 26, 2021   (JP) .................................. 2021-029753

(51) Int. Cl.
*A61B 5/00*    (2006.01)

(52) U.S. Cl.
CPC .......... *A61B 5/7289* (2013.01); *A61B 5/0004* (2013.01); *A61B 5/0006* (2013.01); *A61B 5/002* (2013.01); *A61B 5/6802* (2013.01); *A61B 5/7246* (2013.01); *A61B 5/743* (2013.01)

(58) Field of Classification Search
CPC .................................................. A61B 5/7289
See application file for complete search history.

(56) References Cited

U.S. PATENT DOCUMENTS

| | | | |
|---|---|---|---|
| 2004/0113771 A1 | 6/2004 | Ozaki et al. | |
| 2014/0051947 A1* | 2/2014 | Snyder | A61B 5/0022 600/300 |
| 2017/0181628 A1* | 6/2017 | Burnette | A61B 5/0022 |
| 2018/0153482 A1* | 6/2018 | Watanabe | A61B 5/02055 |

FOREIGN PATENT DOCUMENTS

| | | |
|---|---|---|
| JP | 2004216125 | 8/2004 |
| JP | 2014036747 | 2/2014 |
| JP | 2014036747 A * | 2/2014 |
| JP | 2018027140 | 2/2018 |
| WO | 2018104991 | 6/2018 |

* cited by examiner

*Primary Examiner* — William J Levicky
(74) *Attorney, Agent, or Firm* — JCIPRNET (57) ABSTRACT

A biological information detection system includes a wearable biological information detection device, a stationary biological information detection device, and a control unit. When data from the stationary biological information detection device is received by a first communication unit, the control unit calculates a correlation value between first biological information detected by a first detection unit and second biological information included in the data, and when the calculated correlation value satisfies a predetermined correlation condition, the control unit causes the wearable biological information detection device to start monitoring the second biological information included in the data, as biological information of a wearer.

15 Claims, 6 Drawing Sheets

| Block | Name | Offset | Value | Detail |
|---|---|---|---|---|
| Block 1 | AD Structure Length | +0x00 | 0x02 | DATA LENGTH OF BLOCK 1 = 2 byte |
| | AD type | +0x01 | 0x01 | 0x01: AD type = SPECIFY PACKET TYPE BY Flags |
| | AD Flags | +0x02 | 0x04 | bit 0 (OFF) LE Limited Discoverable Mode<br>bit 1 (ON) LE General Discoverable Mode<br>bit 2 (OFF) BR/EDR Not Supported<br>bit 3 (ON) Simultaneous LE and BR/EDR to Same Device Capable (controller)<br>bit 4 (ON) Simultaneous LE and BR/EDR to Same Device Capable (Host) |
| Block 2 FIRST PERSON | AD Structure Length | +0x03 | 0x08 | DATA LENGTH OF BLOCK 1 = 8 byte |
| | AD type | +0x04 | 0xFF | 0x16: Service Data |
| | Service UUID | +0x05 | 0x0D<br>0x18 | 0x180D: Heart Rate |
| | Heart Rate | +0x07 | 0x43 | 0x43: 67 bpm (EXPRESSED BY HEXADECIMAL NUMBER) |
| | RRI 1 | +0x08 | 0x6C<br>0x03 | 0x036C: 876 msec<br>(EXPRESSED BY HEXADECIMAL NUMBER) |
| | RRI 2 | +0x0A | 0x9f<br>0x03 | 0x039F: 927 msec<br>(EXPRESSED BY HEXADECIMAL NUMBER) |
| Block 3 SECOND PERSON | AD Structure Length | +0x0B | 0x08 | DATA LENGTH OF BLOCK 1 = 8 byte |
| | AD type | +0x0C | 0xFF | 0x16: Service Data |
| | Service UUID | +0x0D | 0x0D<br>0x18 | 0x180D: Heart Rate |
| | Heart Rate | +0x0F | 0x46 | 0x46: 70 bpm (EXPRESSED BY HEXADECIMAL NUMBER) |
| | RRI 1 | +0x10 | 0x6C<br>0x03 | 0x0357: 855 msec (HEXADECIMAL NUMBER) |
| | RRI 2 | +0x12 | 0x48<br>0x03 | 0x0348: 840 msec (HEXADECIMAL NUMBER) |

FIG. 3

| VITAL SIGNS DATA OF WEARABLE DEVICE 10A | VITAL SIGNS DATA OF VITAL SIGNS MONITOR 20 (BLOCK 2) | VITAL SIGNS DATA OF VITAL SIGNS MONITOR (BLOCK 3) |
|---|---|---|
| 875 | 876 | 855 |
| 916 | 927 | 840 |
| 933 | 940 | 832 |
| 922 | 928 | 850 |
| 911 | 912 | 834 |
| 923 | 924 | 855 |
| 943 | 944 | 868 |
| 933 | 935 | 900 |
| 943 | 947 | 911 |
| 932 | 938 | 922 |
| 910 | 920 | 933 |
| 922 | 926 | 965 |
| 899 | 899 | 993 |
| 907 | 911 | 923 |
| CORRELATION COEFFICIENT | 0.983740109 | −0.083655307 |
| AVERAGE OF DIFFERENCE ABSOLUTE VALUES | 4.142857143 | 52.85714286 |

BIOLOGICAL INFORMATION DETECTION SYSTEM, WEARABLE BIOLOGICAL INFORMATION DETECTION DEVICE, AND BIOLOGICAL INFORMATION DETECTION METHOD

The present application is based on, and claims priority from JP Application Serial Number 2021-029753, filed Feb. 26, 2021, the disclosure of which is hereby incorporated by reference herein in its entirety.

BACKGROUND

1. Technical Field

The present disclosure relates to a biological information detection system, a wearable biological information detection device, and a biological information detection method.

2. Related Art

JP-A-2014-036747 discloses a technology in which a biological information measurement device that stores specific biological information associated with identification information of a subject communicates with another biological information measurement device that stores other biological information associated with identification information, in order to compare the identification information associated with the specific biological information with the identification information associated with the other biological information. When both the pieces of identification information match each other, the biological information measurement device acquires the other biological information, and stores the other biological information in association with the identification information that matches the acquired other biological information.

In the technology disclosed in JP-A-2014-036747, in order to centrally manage a plurality of the pieces of biological information of the same subject, which have been measured separately by a plurality of the biological information measurement devices, in association with that subject, it is necessary to perform a cumbersome task of registering, in advance, the identification information (such as a user ID) of all the subjects who use the system.

SUMMARY

In order to solve the problem described above, a biological information detection system according to an aspect of the present disclosure includes a wearable biological information detection device, a stationary biological information detection device, and a control unit. The wearable biological information detection device includes a first detection unit configured to detect first biological information, the first biological information being biological information of a wearer, and a first communication unit configured to communicate with the stationary biological information detection device. The stationary biological information detection device includes a second detection unit configured to detect second biological information, the second biological information being biological information of a subject, and a second communication unit configured to transmit data including the second biological information. When the data is received by the first communication unit, the control unit calculates a correlation value between the first biological information detected by the first detection unit and the second biological information included in the data, and, when the calculated correlation value satisfies a predetermined correlation condition, causes the wearable biological information detection device to start monitoring the second biological information included in the data, as the biological information of the wearer.

A wearable biological information detection device according to an aspect of the present disclosure includes a first detection unit configured to detect first biological information, the first biological information being biological information of a wearer, a first communication unit configured to communicate with a stationary biological information detection device configured to detect second biological information, the second biological information being biological information of a subject, and a control unit configured, when data from the stationary biological information detection device is received by the first communication unit, to calculate a correlation value between the first biological information detected by the first detection unit and the second biological information included in the data, and, when the calculated correlation value satisfies a predetermined correlation condition, to cause the wearable biological information detection device to start monitoring the second biological information included in the data as the biological information of the wearer.

A biological information detection method according to an aspect of the present disclosure uses a wearable biological information detection device configured to detect biological information of a wearer as first biological information, and a stationary biological information detection device configured to detect biological information of a subject as second biological information. The method includes, when data from the stationary biological information detection device is received by the wearable biological information detection device, calculating a correlation value between the first biological information detected by the wearable biological information detection device, and the second biological information included in the data, and, when the calculated correlation value satisfies a predetermined correlation condition, causing the wearable biological information detection device to start monitoring the second biological information included in the data, as the biological information of the wearer.

DESCRIPTION OF EXEMPLARY EMBODIMENTS

An embodiment of the present disclosure will be described below with reference to the accompanying drawings.

Note that, in the drawings, the dimensions of some components may be scaled differently for ease of understanding for each of the components.

Figure 1:
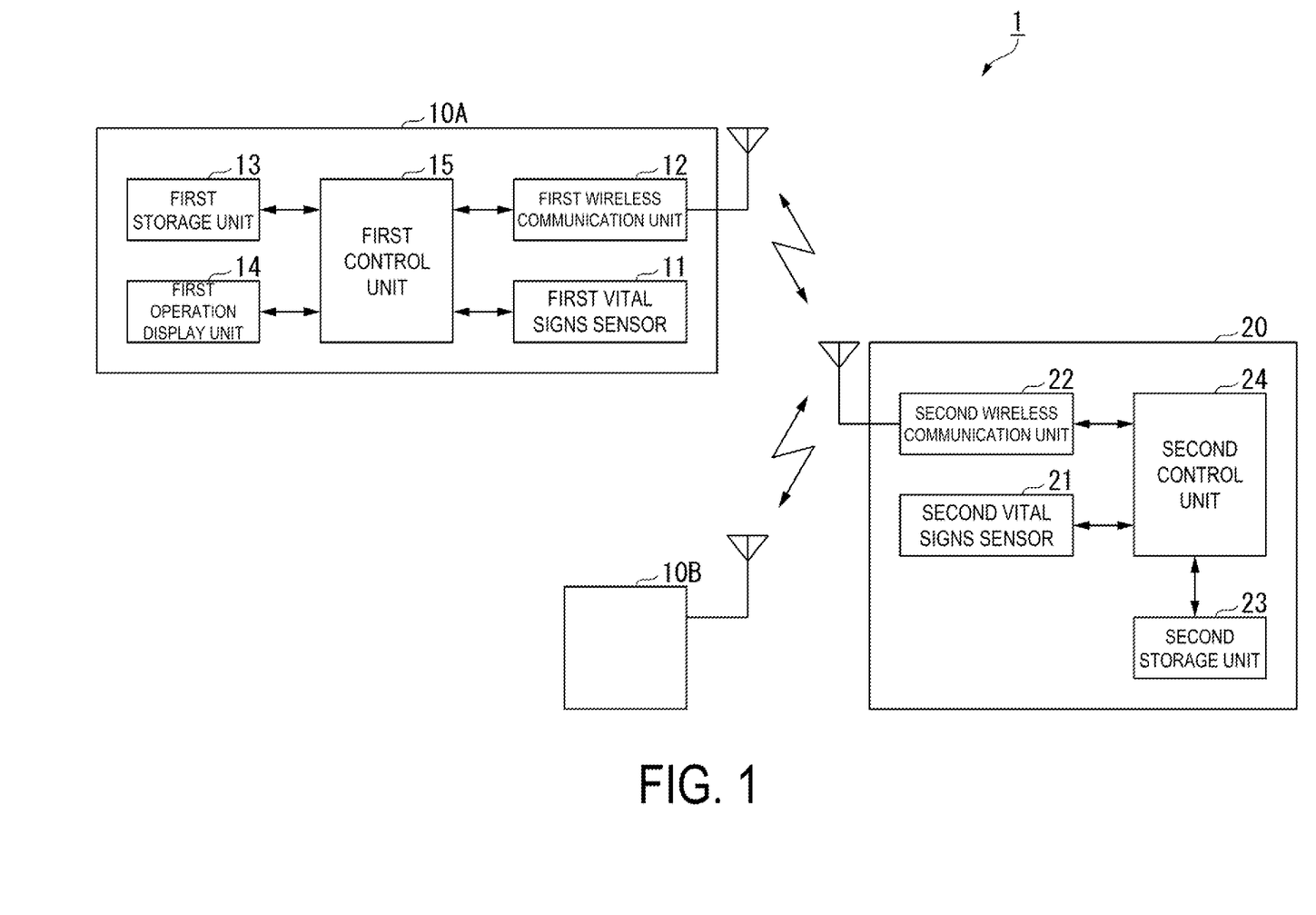
FIG. 1 is a block diagram schematically illustrating a configuration of a biological information detection system according to an embodiment.

FIG. 1 is a block configuration diagram schematically illustrating a biological information detection system 1 according to an embodiment of the present disclosure. As illustrated in FIG. 1, the biological information detection system 1 according to the embodiment includes wearable biological information detection devices 10A and 10B, a stationary biological detection device 20, and a first control unit 15 that functions as a control unit. In the biological information detection system 1 according to the embodiment, a mode is illustrated in which a control unit according to the present disclosure is provided in a wearable biological information detection device.

The wearable biological detection devices 10A and 10B are wearable devices, such as an activity tracker and a smart watch, worn by a subject on their wrist or the like, for example. The wearable biological information detection devices 10A and 10B each include a vital signs sensor such as a photoelectric pulse wave sensor, and detect biological information, such as a heart rate and RRI (R-R Interval), of the subject. In the embodiment, a subject wearing the wearable biological information detection device 10A is referred to as a wearer A, and a subject wearing the wearable biological information detection device 10B is referred to as a wearer B. In the following description, the wearable biological detection devices 10A and 10B may be referred to as wearable devices.

The stationary biological information detection device 20 is a stationary vital signs monitor installed in a predetermined space, such as inside a room or a vehicle, for example. The stationary biological information detection device 20 is equipped with a vital signs sensor such as a millimeter wave radar, for example, and detects the biological information, such as the heart rate and the RRI, of the subject present in the same space. The stationary biological information detection device 20 can detect the biological information of a plurality of the subjects. For example, when the wearer A of the wearable device 10A and the wearer B of the wearable device 10B are present in the space in which the stationary biological information detecting device 20 is installed, the stationary biological information detection device 20 can detect biological information of the wearer A and biological information of the wearer B.

However, the stationary biological information detection device 20 cannot identify that, of two pieces of the detected biological information, one piece of the biological information is the biological information of the "wearer A" and the other piece of the biological information is the biological information of the "wearer B". Here, it should be noted that the stationary biological information detection device 20 simply acquires, of the two pieces of detected biological information, the one piece of biological information as biological information of "a first person of two persons present in the same space", and acquires the other piece of biological information as biological information of "a second person of the two persons present in the same space".

As will be described in detail below, the stationary biological information detection device 20 according to the embodiment functions as a Bluetooth Low Energy (BLE) beacon. In the following description, the stationary biological information detection device 20 may be referred to as a vital signs monitor. Hereinafter, for convenience of explanation, first, a configuration of the vital signs monitor 20 will be described. As illustrated in FIG. 1, the vital signs monitor 20 includes a second vital signs sensor 21 (a second detection unit), a second wireless communication unit 22 (a second communication unit), a second storage unit 23, and a second control unit 24.

The second vital signs sensor 21 is a vital signs sensor that detects second biological information, which is the biological information of the subject present in the space in which the vital signs monitor 20 is installed. The second vital signs sensor 21 is, for example, a millimeter wave radar, and detects the biological information, such as the heart rate and the RRI, of the subject as the second biological information. The second vital signs sensor 21 can detect the biological information of a plurality of the subjects. The second vital signs sensor 21 outputs the detected second biological information to the second control unit 24. In the following description, the second biological information may be referred to as second vital signs data.

The second wireless communication unit 22 is a BLE transmitter receiver that wirelessly communicates with other devices in accordance with the BLE standard, which is a near field communication standard. For example, when the wearable devices 10A and 10B are present in the space in which the vital signs monitor 20 is installed, the second wireless communication unit 22 wirelessly communicates with the wearable devices 10A and 10B in accordance with the BLE standard. The second wireless communication unit 22 transmits an advertising packet as data including the second vital signs data at a predetermined time interval (a one second interval, for example) under control of the second control unit 24. In other words, the vital signs monitor 20 functions as the BLE beacon. The advertising packet corresponds to a beacon packet in the present disclosure. The beacon packet is a packet that is receivable by an unspecified large number of devices operating in accordance with the same communication standard as that of the vital signs monitor 20.

The second storage unit 23 includes a non-volatile memory that stores programs and various setting values necessary to cause the second control unit 24 to perform various processing, and a volatile memory that is used as a temporary data storage location when the second control unit 24 performs the various processing. The non-volatile memory is, for example, an electrically erasable programmable read-only memory (EEPROM), a flash memory, or the like. The volatile memory is, for example, a random access memory (RAM). The second storage unit 23 stores the second vital signs data as necessary under the control of the second control unit 24.

The second control unit 24 is, for example, a microprocessor such as a central processing unit (CPU) or a micro controller unit (MCU). The second control unit 24 controls an overall operation of the vital signs monitor 20 in accordance with the program stored in the second storage unit 23. For example, the second control unit 24 activates the second vital signs sensor 21 to cause the second vital signs sensor 21 to start detecting the second vital signs data. Further, the second control unit 24 controls the second wireless communication unit 22 so as to cause the second wireless communication unit 22 to transmit the advertising packet including the second vital signs data detected by the second vital signs sensor 21 at the one second interval.

The wearable device 10A includes a first vital signs sensor 11 (a first detection unit), a first wireless communication unit 12 (a first communication unit), a first storage unit 13 (a first storage unit), a first operation display unit 14 (a first notification unit), and the first control unit 15 (a control unit). Since the wearable device 10B has the same configuration as that of the wearable device 10A, a description of the configuration of the wearable device 10B will be omitted.

The first vital signs sensor 11 is a vital signs sensor that detects first biological information, which is the biological information of the wearer A wearing the wearable device 10A. The first vital signs sensor 11 is, for example, a photoelectric pulse wave sensor, and detects the biological information, such as the heart rate and the RRI, of the subject as the first biological information. The first vital signs sensor 11 outputs the detected first biological information to the first control unit 15. In the following description, the first biological information may be referred to as first vital signs data.

The first wireless communication unit 12 is a BLE transmitter receiver that wirelessly communicates with other devices in accordance with the BLE standard. For example, when the wearable device 10A is present in the space in which the vital signs monitor 20 is installed, the first wireless communication unit 12 wirelessly communicates with the vital signs monitor 20 in accordance with the BLE standard. The first wireless communication unit 12 receives the advertising packet transmitted from the vital signs monitor 20 at the one second interval, by performing scanning under control of the first control unit 15.

The first storage unit 13 includes a non-volatile memory that stores programs and various setting values necessary to cause the first control unit 15 to perform various processing, and a volatile memory that is used as a temporary data storage location when the first control unit 15 performs the various processing. The non-volatile memory is, for example, an EEPROM, a flash memory, or the like. The volatile memory is, for example, a RAM.

The first operation display unit 14 is a touch panel type display device. The wearer A can input an instruction to the wearable device 10A by operating the first operation display unit 14. The first operation display unit 14 outputs, as an operation signal, an electrical signal that is generated in accordance with an operation of a touch panel by the wearer A, to the first control unit 15. Further, the first operation display unit 14 displays a predetermined image on the touch panel based on an image signal input from the first control unit 15.

The first control unit 15 is, for example, a microprocessor such as a CPU or a MCU. The first control unit 15 controls an overall operation of the wearable device 10A in accordance with the program stored in the first storage unit 13. For example, when an operation signal instructing a start of sensing is input from the first operation display unit 14, the first control unit 15 activates the first vital signs sensor 11 to cause the first vital signs sensor 11 to start detecting the first vital signs data. Further, the first control unit 15 controls the first wireless communication unit 12 so as to cause the first wireless communication unit 12 to perform scanning of the advertising packet.

As will be described in detail below, when the advertising packet from the vital signs monitor 20 is received from the first wireless communication unit 12, the first control unit 15 calculates a correlation value between the first vital signs data detected by the first vital signs sensor 11 and the second vital signs data included in the advertising packet, and when the calculated correlation value satisfies a predetermined correlation condition, the first control unit 15 causes the wearable device 10A to start monitoring the second vital signs data included in the advertising packet as the biological information of the wearer A. In particular, when the second vital signs data of a plurality of the subjects are included in the advertising packet, the first control unit 15 calculates the correlation value between the first vital signs data and the second vital signs data for each of the plurality of subjects, and the first control unit 15 causes the wearable device 10A to start monitoring the second vital signs data corresponding to the correlation value that has satisfied the correlation condition, of the calculated correlation values.

In the embodiment, as described above, a state in which the monitoring of the second vital signs data is being performed by the wearable device 10A, the second vital signs data being included in the advertising packet as the biological information of the wearer A, may be expressed as a state in which a link between the wearable device 10A and the vital signs monitor 20 is established. In other words, the state in which the link between the wearable device 10A and the vital signs monitor 20 is established is a state in which the second vital signs data of one of the subjects, of the second vital signs data of the plurality of subjects detected by the vital signs monitor 20, is associated with the wearer A as the biological information of the wearer A of the wearable device 10A.

Figure 2:
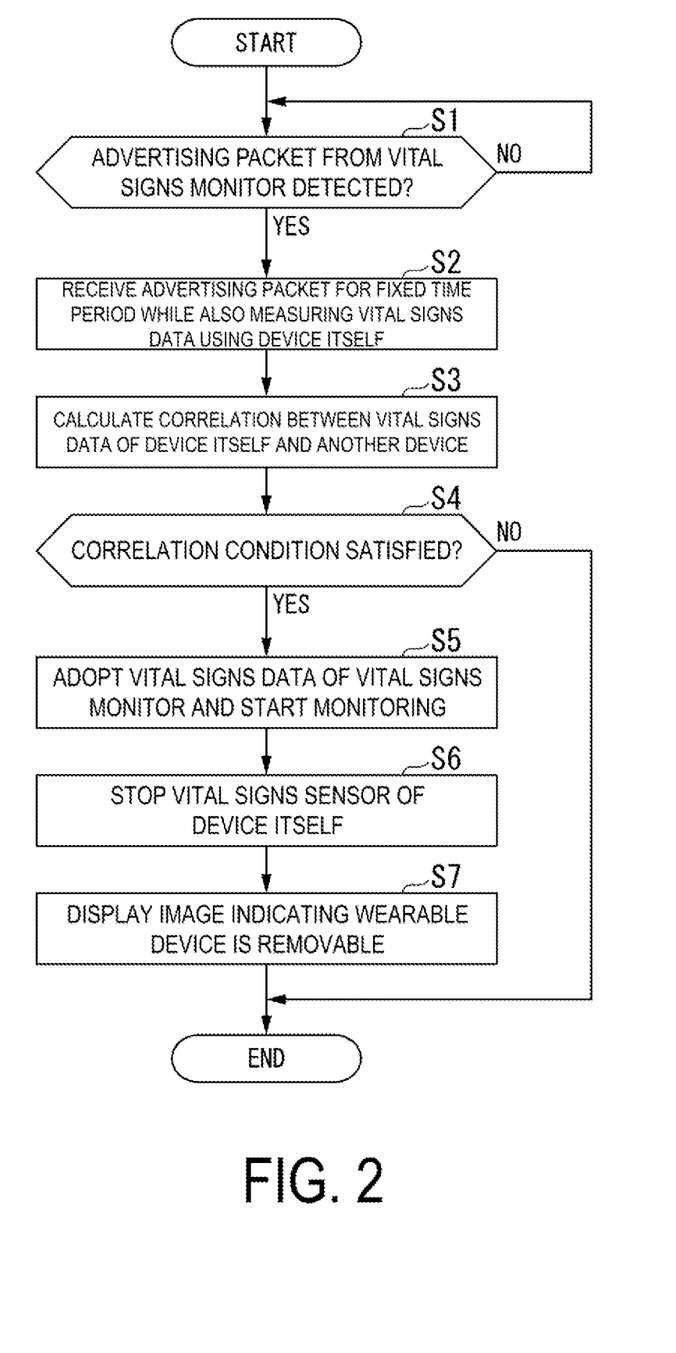
FIG. 2 is a flowchart illustrating an operation of a wearable device in a link initiation phase of the biological information detection system according to the embodiment.

FIG. 2 is a flowchart illustrating an operation of the wearable device 10A in a link initiation phase of the biological information detection system 1. The link initiation phase is a phase that includes processing from when the wearable device 10A receives the advertising packet, to when the monitoring is started of the second vital signs data included in the advertising packet as the biological information of the wearer A. In other words, the link initiation phase is a phase that includes processing from when the wearable device 10A receives the advertising packet, to when a transition is complete to the state in which the link between the wearable device 10A and the vital signs monitor 20 is established.

As illustrated in FIG. 2, in the link initiation phase, the first control unit 15 of the wearable device 10A determines whether the advertising packet from the vital signs monitor 20 has been received (detected) by the scanning operation of the first wireless communication unit 12 (step S1). When "NO" at step S1, that is, when the advertising packet from the vital signs monitor 20 has not been received by the scanning operation of the first wireless communication unit 12, it is presumed that the wearable device 10A is not present in the space in which the vital signs monitor 20 is installed. Thus, in this case, the first control unit 15 repeats the processing at step S1 at a predetermined time interval. The time interval at which the processing at step S1 is repeated is preferably the same as the time interval at which the advertising packet is transmitted by the vital signs monitor 20.

While repeating the processing at step S1, the first control unit 15 acquires the first vital signs data detected by the first vital signs sensor 11 as the biological information of the wearer A, and stores the acquired first vital signs data in the first storage unit 13. At the same time, the first control unit 15 generates an image signal indicating a pulsation waveform, the heart rate, the RRI, and the like of the wearer A, based on time series data of the first vital signs data stored in the first storage unit 13, and outputs the image signal to the first operation display unit 14. As a result, during a period in which the advertising packet from the vital signs monitor 20 is not received by the scanning operation of the first wireless communication unit 12, the image indicating the pulsation waveform, the heart rate, the RRI, and the like of the wearer A based on the first vital signs data is displayed on the touch panel of the first operation display unit 14.

When it is "YES" at step S1 described above, that is, when the advertising packet from the vital signs monitor 20 has been received by the scanning operation of the first wireless communication unit 12, it is presumed that the wearable device 10A has entered the space in which the vital signs monitor 20 is installed. In this case, while continuing storing, in the first storage unit 13, the first vital signs data detected by the first vital signs sensor 11 as the biological information of the wearer A, the first control unit 15 receives the advertising packet transmitted from the vital signs monitor 20 at the one second interval for a fixed time period (step S2). The first control unit 15 extracts the second vital signs data from a plurality of the advertising packets received within the fixed time period, and stores the extracted plurality of second vital signs data in the first storage unit 13.

Figure 3:
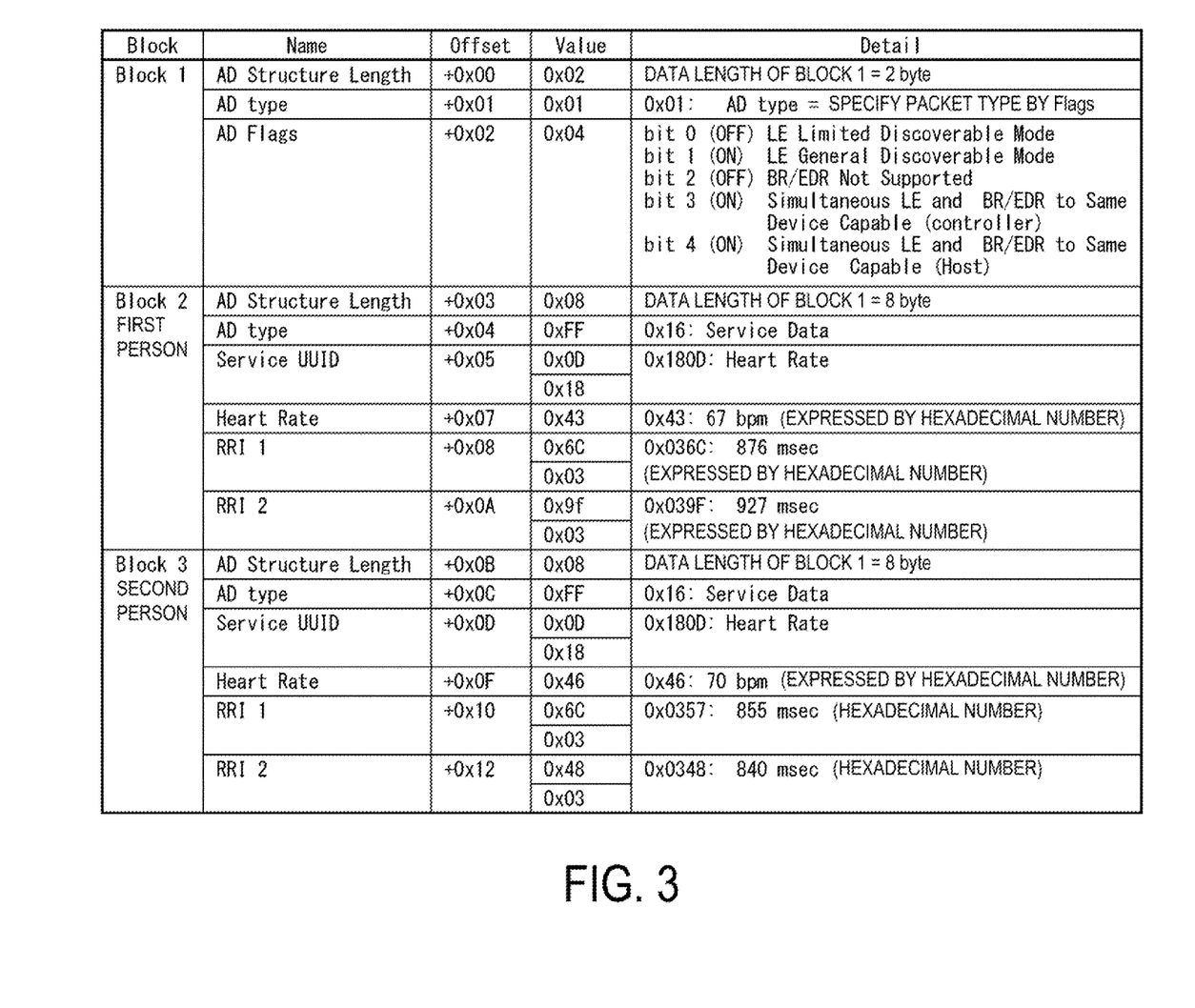
FIG. 3 is a diagram illustrating an example of a format of an advertising packet transmitted from a vital signs monitor according to the embodiment.

FIG. 3 is a diagram illustrating an example of a format of the advertising packet transmitted from the vital signs monitor 20. As illustrated in FIG. 3, the advertising packet is constituted by a plurality of blocks. In an example illustrated in FIG. 3, the advertising packet is constituted by three blocks. Of the three blocks constituting the advertising packet, Block 1 stores data indicating that this packet is an advertising packet defined by the BLE standard. Note that in FIG. 3, "Name" represents a name of stored data. "Offset" represents a location at which the data indicated by "Name" is stored, in terms of a location (byte) from the top of the advertising packet. "Value" represents a numerical value of the data stored at the location indicated by "Offset". "Detail" is a description of each of the numerical values, and is not included in the advertising packet actually transmitted.

In the link initiation phase, when both the wearable devices 10A and 10B enter the space in which the vital signs monitor 20 is installed, the second vital signs sensor 21 of the vital signs monitor 20 detects the second vital signs data as the biological information of "the first person of the two persons present in the same space", and the second vital signs data as the biological information of "the second person of the two persons present in the same space". As illustrated in FIG. 3, for example, the second control unit 24 of the vital signs monitor 20 stores the second vital signs data of the first subject in Block 2, and stores the second vital signs data of the second subject in Block 3, of the three blocks constituting the advertising packet. In the following description, the first person may be referred to as the first subject, and the second person may be referred to as the second subject.

As an example, in Block 2, "0×43" is stored as a numerical value indicating the heart rate of the first subject at the location "Heart Rate". "0×43" indicates that the heart rate is 67 bpm. As an example, in Block 2, "0×036C" is stored as a numerical value indicating the RRI of the first subject at the location "RRI1", and "0×039F" is stored as a numerical value indicating the RRI of the first subject at the location "RRI2". "0×036C" indicates that the RRI is 876 msec, and "0×039F" indicates that the RRI is 927 msec.

As an example, in Block 3, "0×46" is stored as a numerical value indicating the heart rate of the second subject at the location "Heart Rate". "0×46" indicates that the heart rate is 70 bpm. As an example, in Block 3, "0×0357" is stored as a numerical value indicating the RRI of the second subject at the location "RRI1", and "0×0348" is stored as a numerical value indicating the RRI of the second subject at the location "RRI2". "0×0357" indicates that the RRI is 855 msec, and "0×0348" indicates that the RRI is 840 msec.

In the embodiment, the advertising packet is transmitted from the vital signs monitor 20 at a one second interval, for example. Thus, when the heart rate is higher than 60 bpm, as illustrated in FIG. 3, a plurality of the RRIs may be obtained for each of the subjects within one second. On the other hand, when the heart rate is lower than 60 bpm, no RRI may be obtained for each of the subjects within one second.

As described above, in the link initiation phase, when the wearable devices 10A and 10B have entered the space in which the vital signs monitor 20 is installed, the advertising packet, in which the second vital signs data of the first subject is stored in Block 2 and the second vital signs data of the second subject is stored in Block 3, is transmitted from the vital signs monitor 20 at the one second interval.

At step S2, while continuing storing, in the first storage unit 13, the first vital signs data detected by the first vital signs sensor 11 as the biological information of the wearer A, the first control unit 15 extracts the second vital signs data of the first subject and the second vital signs data of the second subject from the plurality of advertising packets received within the fixed time period, and stores the extracted plurality of second vital signs data in the first storage unit 13.

Figure 4:
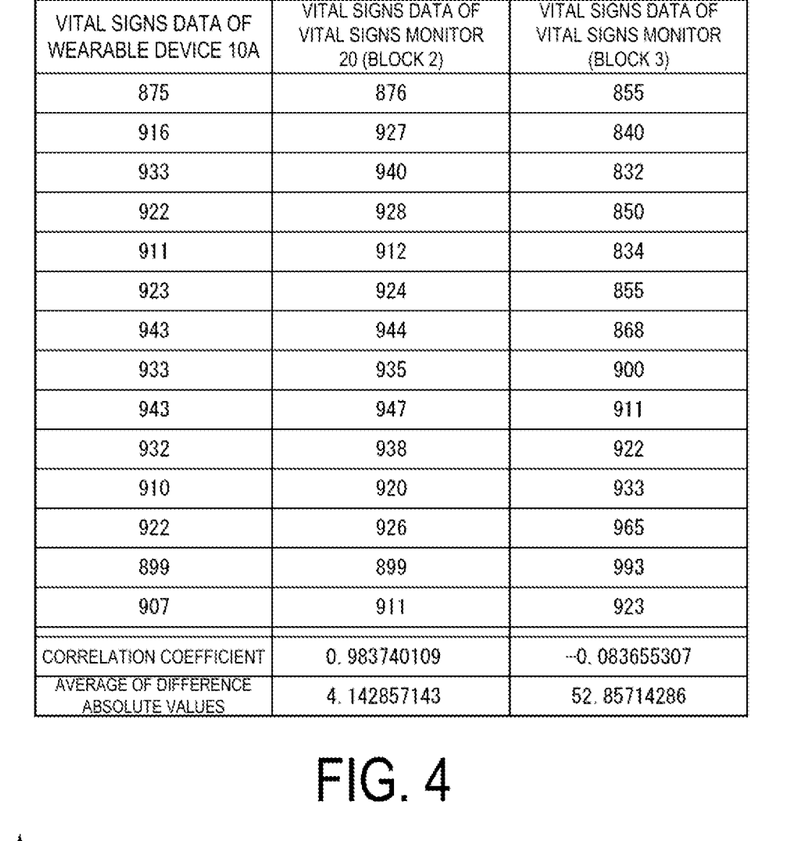
FIG. 4 is an explanatory diagram relating to the operation of the wearable device in the link initiation phase.
Figure 5:
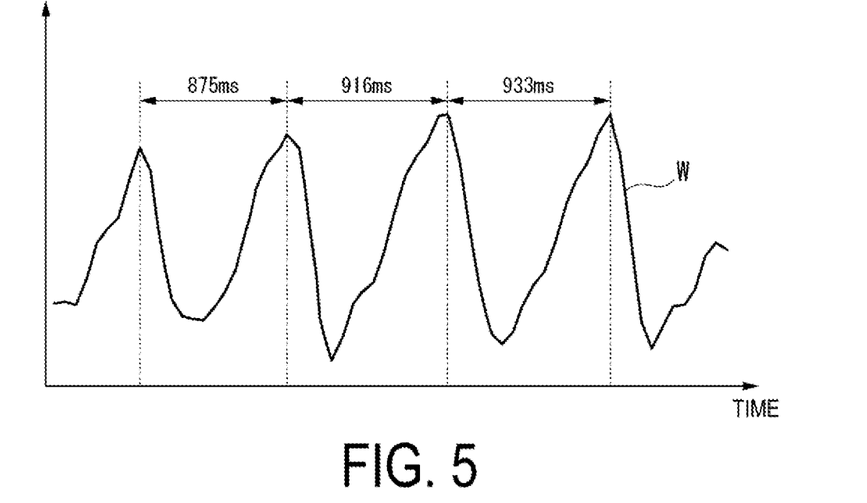
FIG. 5 is an explanatory diagram relating to RRI, which is a type of biological information.

As a result, as illustrated in FIG. 4, time series data of the first vital signs data of the wearer A detected within the fixed time period, time series data of the second vital signs data of the first subject detected within the fixed time period (the second vital signs data stored in Block 2), and time series data of the second vital signs data of the second subject detected within the fixed time period (the second vital signs data stored in Block 3) are stored in the first storage unit 13. Note that in FIG. 4, only the RRI is illustrated as each of the vital signs data. FIG. 5 is a diagram illustrating a portion of time series data of the RRI of the wearer A, using a pulsation waveform W. As illustrated in FIG. 5, of a plurality of peaks appearing in the pulsation waveform W, the RRI is a time period between a pair of the peaks adjacent to each other.

Referring to FIG. 2 again, the first control unit 15 of the wearable device 10A calculates, based on the time series data of each of the vital signs data stored in the first storage unit 13, the correlation value between the first vital signs data detected by the first vital signs sensor 11 and the second vital signs data included in the advertising packet (step S3). When the second vital signs data of the plurality of subjects are included in the advertising packet as in the embodiment, the first control unit 15 calculates the correlation value between the first vital signs data and the second vital signs data for each of the plurality of subjects.

Specifically, the first control unit 15 calculates the correlation value between the first vital signs data of the wearer A and the second vital signs data of the first subject, based on the time series data of the first vital signs data of the wearer A and the time series data of the second vital signs data of the first subject, both of which are stored in the first storage unit 13. Further, the first control unit 15 calculates the correlation value between the first vital signs data of the wearer A and the second vital signs data of the second subject, based on the time series data of the first vital signs data of the wearer A and the time series data of the second vital signs data of the second subject, both of which are stored in the first storage unit 13.

The correlation value includes at least one of a correlation coefficient and an average of difference absolute values. As illustrated in FIG. 4, in the embodiment, as an example, both the correlation coefficient and the average of difference absolute values are calculated as the correlation value. A method of calculating the correlation coefficient and the average of difference absolute values is known, and thus, a description of the method is omitted herein. In an example illustrated in FIG. 4, approximately 0.983 is calculated as the correlation coefficient between the first vital signs data of the wearer A and the second vital signs data of the first subject, and approximately 4.142 is calculated as the average of difference absolute values between the first vital signs data of the wearer A and the second vital signs data of the first subject. Further, in the example illustrated in FIG. 4, approximately −0.083 is calculated as the correlation coefficient between the first vital signs data of the wearer A and the second vital signs data of the second subject, and approximately 52.857 is calculated as the average of difference absolute values between the first vital signs data of the wearer A and the second vital signs data of the second subject.

Referring to FIG. 2 again, the first control unit 15 of the wearable device 10A determines whether the correlation value calculated at step S3 described above satisfies the predetermined correlation condition (step S4). When it is "NO" at step S4, that is, when the correlation value calculated at step S3 does not satisfy the predetermined correlation condition, the first control unit 15 terminates the operation illustrated in FIG. 2. In this case, the first control unit 15 continues to generate the image signal indicating the pulsation waveform, the heart rate, the RRI, and the like of the wearer A based on the time series data of the first vital signs data acquired from the first vital signs sensor 11, and outputs the generated image signal to the first operation display unit 14. As a result, even after the operation illustrated in FIG. 2 is terminated, the image indicating the pulsation waveform, the heart rate, the RRI, and the like of the wearer A based on the first vital signs data is displayed on the touch panel of the first operation display unit 14.

On the other hand, when it is "YES" at step S4 described above, that is, when the correlation value calculated at step S3 satisfies the predetermined correlation condition, the first control unit 15 causes the wearable device 10A to start monitoring the second vital signs data included in the advertising packet as the biological information of the wearer A (step S5). When the second vital signs data of the plurality of subjects are included in the advertising packet as in the embodiment, the first control unit 15 causes the wearable device 10A to start monitoring the second vital signs data corresponding to the correlation value that satisfies the predetermined correlation condition, of the correlation values calculated at step 3.

The predetermined correlation condition includes at least one of a first correlation condition that is, among the correlation coefficients calculated respectively for the plurality of subjects, a correlation coefficient greater than a first threshold value, a second correlation condition that is, among the averages of difference absolute values calculated respectively for the plurality of subjects, an average of difference absolute values smaller than a second threshold value, a third correlation condition that is a largest correlation coefficient among the correlation coefficients calculated respectively for the plurality of subjects, and a fourth correlation condition that the average of difference absolute values is smallest among the averages of difference absolute values calculated respectively for the plurality of subjects. As an example, the first threshold is 0.90, and the second threshold is 20.

In the example illustrated in FIG. 4, the correlation value (the correlation coefficient and the average of difference absolute values) between the first vital signs data of the wearer A and the second vital signs data of the first subject satisfies all the correlation conditions from the first correlation condition to the fourth correlation condition. In this case, at step S5, the first control unit 15 causes the wearable device 10A to start monitoring the second vital signs data of the first subject, for which the correlation values satisfying all the correlation conditions have been obtained. Specifically, after determining Block 2, which stores the second vital signs data of the first subject, as the block to be monitored among the three blocks constituting the advertising packet, each time the advertising packet from the vital signs monitor 20 is received by the scanning operation of the first wireless communication unit 12 at the one second interval, the first control unit 15 acquires the second vital signs data stored in Block 2, which is the block to be monitored in the advertising packet, as the biological information of the wearer A.

As a result of the processing from step S1 to step S5 described above, the link between the wearable device 10A and the vital signs monitor 20 is established. In other words, of the second vital signs data of the two subjects detected by the vital signs monitor 20, the second vital signs data of the first subject is associated with the wearer A as the biological information of the wearer A of the wearable device 10A.

The first control unit 15 stores the second vital signs data acquired from Block 2, which is the block to be monitored in the advertising packet, in the first storage unit 13 as the biological information of the wearer A, as described above, and at the same time, stops the operation of the first vital signs sensor 11 (step S6). In this way, after the monitoring is started, the first storage unit 13 stores the second vital signs data included in the advertising packet received by the first wireless communication unit 12. Further, after the monitoring is started, the first vital signs sensor 11 stops detecting the first vital signs data of the wearer A.

Then, by outputting a predetermined image signal to the first operation display unit 14, the first control unit 15 displays an image indicating that the wearable device 10A is removable, on the touch panel of the first operation display unit 14 (step S7). In this way, after the monitoring is started, the first operation display unit 14 notifies the wearer A that the wearable device 10A is removable.

Although the operation of the wearable device 10A in the link initiation phase is described above, an operation of the wearable device 10B in the link initiation phase is also the same as the operation illustrated in FIG. 2. For example, when the correlation value between the first vital signs data of the wearer B detected by the first vital signs sensor 11 and the second vital signs value of the second subject included in the advertising packet received from the vital signs monitor 20 satisfies the correlation condition, the first control unit 15 of the wearable device 10B causes the wearable device 10B to start monitoring the second vital signs data of the second subject included in the advertising packet.

Specifically, in this case, after determining Block 3, which stores the second vital signs data of the second subject, as the block to be monitored among the three blocks constituting the advertising packet, each time the advertising packet is received from the vital signs monitor 20 at the one second interval, the first control unit 15 of the wearable device 10B acquires the second vital signs data stored in Block 3, which is the block to be monitored in the advertising packet, as the biological information of the wearer B. As a result, a link between the wearable device 10B and the vital signs monitor 20 is established. In other words, of the second vital signs data of the two subjects detected by the vital signs monitor 20, the second vital signs data of the second subject is associated with the wearer B as the biological information of the wearer B of the wearable device 10B.

Figure 6:
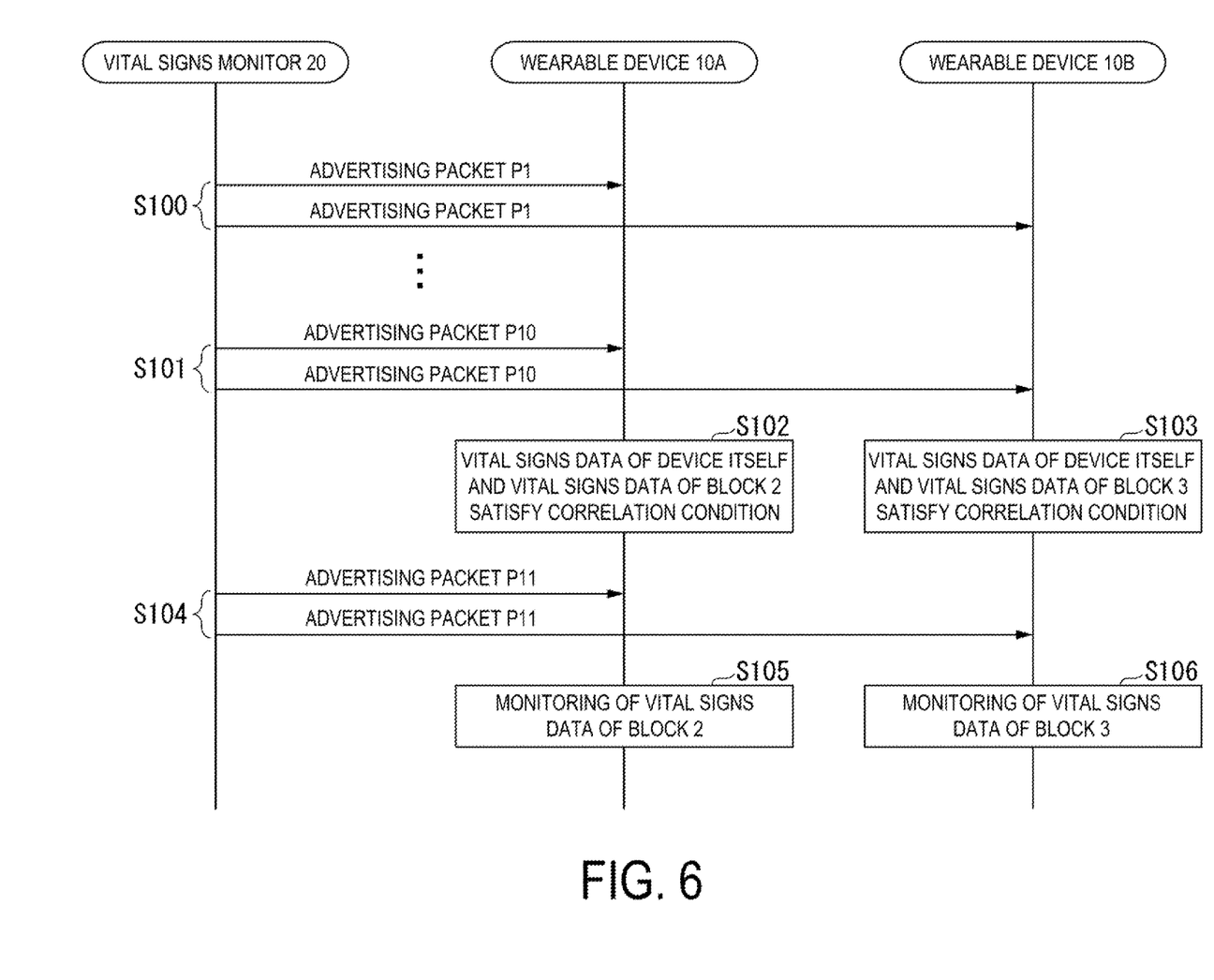
FIG. 6 is a sequence chart illustrating operations of the wearable device and the vital signs monitor in the link initiation phase of the biological information detection system according to the embodiment.

FIG. 6 is a sequence chart illustrating the operations of the wearable devices 10A and 10B in the link initiation phase, and the operation of the vital signs monitor 20. As illustrated in FIG. 6, at step S100, the wearable devices 10A and 10B respectively receive advertising packets P1 transmitted from the vital signs monitor 20, by the scanning operation of the first wireless communication units 12 of each of the wearable devices 10A and 10B.

Upon receiving the first advertising packet P1, the wearable device 10A receives the advertising packets transmitted from the vital signs monitor 20 at the one second interval for the fixed time period, while continuing storing, in the first storage unit 13 of the wearable device 10A, the first vital signs data detected by the first vital signs sensor 11 of the wearable device 10A as the biological information of the wearer A. Each time the wearable device 10A receives the advertising packet at the one second interval, the wearable device 10A extracts, from the received advertising packet, the second vital signs data of the first subject (the second vital signs data stored in Block 2) and the second vital signs data of the second subject (the second vital signs data stored in Block 3), and stores the extracted second vital signs data in the first storage unit 13 of the wearable device 10A.

Similarly, upon receiving the first advertising packet P1, the wearable device 10B receives the advertising packets transmitted from the vital signs monitor 20 at the one second interval for the fixed time period, while continuing storing, in the first storage unit 13 of the wearable device 10B, the first vital signs data detected by the first vital signs sensor 11 of the wearable device 10B as the biological information of the wearer B. Each time the wearable device 10B receives the advertising packet at the one second interval, the wearable device 10B extracts, from the received advertising packet, the second vital signs data of the first subject (the second vital signs data stored in Block 2) and the second vital signs data of the second subject (the second vital signs data stored in Block 3), and stores the extracted second vital signs data in the first storage unit 13 of the wearable device 10B.

At step S101, when the fixed time period elapses at a timing when each of the wearable devices 10A and 10B receives an advertising packet P10 transmitted from the vital signs monitor 20, the wearable devices 10A and 10B respectively calculate the correlation values between the first vital signs data and the second vital signs data for each of the plurality of subjects, based on time series data of each of the vital signs data stored in the first storage units 13 of the wearable devices 10A and 10B.

At step S102, when the wearable device 10A determines that the correlation value between the first vital signs data of the wearer A and the second vital signs data of the first subject (the second vital signs data stored in Block 2) satisfies the correlation condition, the wearable device 10A starts monitoring the second vital signs data included in Block 2 of the advertising packet as the biological information of the wearer A. As a result, the link between the wearable device 10A and the vital signs monitor 20 is established. In other words, of the second vital signs data of the two subjects detected by the vital signs monitor 20, the second vital signs data of the first subject is associated with the wearer A as the biological information of the wearer A of the wearable device 10A.

At step S103, when the wearable device 10B determines that the correlation value between the first vital signs data of the wearer B and the second vital signs data of the second subject (the second vital signs data stored in Block 3) satisfies the correlation condition, the wearable device 10B starts monitoring the second vital signs data included in Block 3 of the advertising packet as the biological information of the wearer B. As a result, a link between the wearable device 10B and the vital signs monitor 20 is established. In other words, of the second vital signs data of the two subjects detected by the vital signs monitor 20, the second vital signs data of the second subject is associated with the wearer B as the biological information of the wearer B of the wearable device 10B.

After the link between the wearable device 10A and the vital signs monitor 20 is established, when the wearable device 10A receives an advertising packet P11 from the vital signs monitor 20 by the scanning operation of the first wireless communication unit 12 of the wearable device 10A at step S104, at step S105, the wearable device 10A acquires the second vital signs data included in Block 2 of the advertising packet P11 as the biological information of the wearer A, and stores the acquired second vital signs data in the first storage unit 13 of the wearable device 10A. After that, the wearable device 10A performs the same operation as the operation at step S105, each time the wearable device 10A receives the advertising packet from the vital signs monitor 20 at the one second interval.

After the link between the wearable device 10B and the vital signs monitor 20 is established, when the wearable device 10B receives the advertising packet P11 from the vital signs monitor 20 by the scanning operation of the first wireless communication unit 12 of the wearable device 10B at step S104, at step S106, the wearable device 10B acquires the second vital signs data included in Block 3 of the advertising packet P11 as the biological information of the wearer B, and stores the acquired second vital signs data in the first storage unit 13 of the wearable device 10B. After that, the wearable device 10B performs the same operation as the operation at step S106 each time the wearable device 10B receives the advertising packet from the vital signs monitor 20 at the one second interval.

Figure 7:
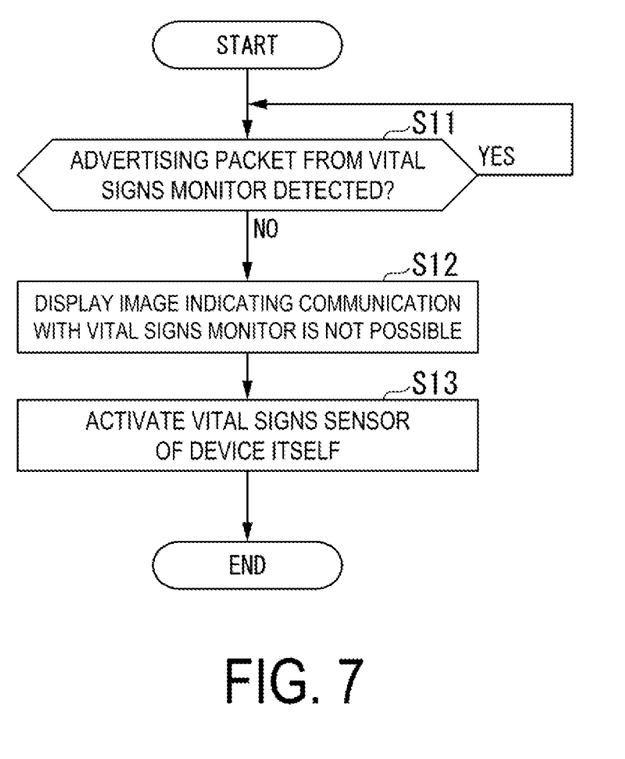
FIG. 7 is a flowchart illustrating an operation of the wearable device in a link cancellation phase of the biological information detection system according to the embodiment.

FIG. 7 is a flowchart illustrating an operation of the wearable device 10A in a link cancellation phase of the biological information detection system 1. As illustrated in FIG. 7, after the monitoring is started, that is, after the link between the wearable device 10A and the vital signs monitor 20 is established, the first control unit 15 of the wearable device 10A determines whether the advertising packet from the vital signs monitor 20 has been received (detected) by the scanning operation of the first wireless communication unit 12 (step S11).

When it is "YES" at step S11 described above, that is, when the advertising packet from the vital signs monitor 20 is received by the scanning operation of the first wireless communication unit 12, it is presumed that the wearable device 10A is present in the space in which the vital signs monitor 20 is installed. In this case, the first control unit 15 continues to receive the advertising packet at the one second interval by the scanning operation of the first wireless communication unit 12, and acquires the second vital signs data stored in Block 2, which is the block to be monitored in the advertising packet, as the biological information of the wearer A.

On the other hand, when it is "NO" at step S11, that is, when the advertising packet from the vital signs monitor 20 has not been received by the scanning operation of the first wireless communication unit 12, it is presumed that the wearable device 10A has moved out of the space in which the vital signs monitor 20 is installed. In this case, the first control unit 15 causes an image indicating that communication with the vital signs monitor 20 has been cut off to be displayed on the touch panel of the first operation display unit 14 by outputting a predetermined image signal to the first operation display unit 14 (step S12), and further, activates the first vital signs sensor 11 (step S13).

As a result of the operation of the wearable device 10A in the link cancellation phase described above, after the link between the wearable device 10A and the vital signs monitor 20 is established, when the advertising packet is not received by the first wireless communication unit 12 of the wearable device 10A, the first operation display unit 14 of the wearable device 10A notifies that the communication with the vital signs monitor 20 has been cut off, and the first vital signs sensor 11 of the wearable device 10A restarts detecting the first vital signs data as the biological information of the wearer A. In this way, the link between the wearable device 10A and the vital signs monitor 20 is canceled.

An operation of the wearable device 10B in the link cancellation phase is also the same as the operation illustrated in FIG. 7. After the link between the wearable device 10B and the vital signs monitor 20 is established, when the advertising packet is not received by the scanning operation of the first wireless communication unit 12, the first control unit 15 causes the image indicating that the communication with the vital signs monitor 20 has been cut off to be displayed on the touch panel of the first operation display unit 14 by outputting the predetermined image signal to the first operation display unit 14, and further, activates the first vital signs sensor 11.

As a result of the operation of the wearable device 10B in the link cancellation phase described above, after the link between the wearable device 10B and the vital signs monitor 20 is established, when the advertising packet is not received by the first wireless communication unit 12 of the wearable device 10B, the first operation display unit 14 of the wearable device 10B notifies that the communication with the vital signs monitor 20 has been cut off, and the first vital signs sensor 11 of the wearable device 10B restarts detecting the first vital signs data as the biological information of the wearer B. In this way, the link between the wearable device 10B and the vital signs monitor 20 is canceled.

As described above, in the embodiment, when the advertising packet from the vital signs monitor 20 is received by the wearable device 10A, the correlation value between the first vital signs data of the wearer A detected by the wearable device 10A and the second vital signs data included in the advertising packet is calculated, and when the calculated correlation value satisfies the predetermined correlation condition, the wearable device 10A is caused to start monitoring the second vital signs data included in the advertising packet as the biological information of the wearer A. In particular, when the second vital signs data of the plurality of subjects are included in the advertising packet as in the embodiment, the correlation value between the first vital signs data and the second vital signs data for each of the plurality of subjects is calculated, and the wearable device 10A is caused to start monitoring the second vital signs data corresponding to the correlation value that has satisfied the correlation condition, of the calculated correlation values.

In this way, without performing a cumbersome task of registering identification information (such as a user ID) of all the subjects who use the system, as in a known technology, among the second vital signs data of the plurality of subjects detected by the vital signs monitor 20, the second vital signs data of one of the subjects is automatically associated with the wearer A as the biological information of the wearer A of the wearable device 10A. As a result, the wearer A of the wearable device 10A can receive services from the vital signs monitor 20 (such as provision of the vital signs data of the wearer A), and even when the wearer A removes the wearable device 10A, the wearable device 10A can continuously collect and record the second vital signs data detected by the vital signs monitor 20 as the biological information of the wearer A. The same effects can also be obtained with the wearable device 10B.

Further, in the embodiment, after the monitoring is started, that is, after the link between the wearable device 10A and the vital signs monitor 20 is established, the first storage unit 13 of the wearable device 10A stores the second vital signs data included in the advertising packet received by the first wireless communication unit 12 of the wearable device 10A, and the first vital signs sensor 11 of the wearable device 10A stops detecting the first vital signs data of the wearer A. Further, the first operation display unit 14 of the wearable device 10A notifies the wearer A that the wearable device 10A is removable.

In this way, even if the wearer A removes the wearable device 10A, it is possible to continuously collect and record the second vital signs data detected by the vital signs monitor 20 as the biological information of the wearer A, while suppressing the power consumption of the wearable device 10A. The same effects can also be obtained with the wearable device 10B.

Further, in the embodiment, after the monitoring is started, that is, after the link between the wearable device 10A and the vital signs monitor 20 is established, when the advertising packet is not received by the first wireless communication unit 12 of the wearable device 10A, the first operation display unit 14 of the wearable device 10A notifies that the communication with the vital signs monitor 20 has been cut off, and the first vital signs sensor 11 of the wearable device 10A restarts detecting the first vital signs data as the biological information of the wearer A.

In this way, even when the communication between the wearable device 10A and the vital signs monitor 20 is cut off, and a state is obtained in which the services from the vital signs monitor 20 cannot be received, it is possible to continuously collect and record the first vital signs data detected by the first vital signs sensor 11 as the biological information of the wearer A. The same effects can also be obtained with the wearable device 10B.

Note that the technical scope of the present disclosure is not limited to the above-described embodiment, and various modifications can be made to the above-described embodiment without departing from the spirit and gist of the present disclosure.

For example, in the embodiment described above, a mode is exemplified in which the control unit (the first control unit 15) according to the present disclosure is provided in the wearable biological information detection device, but the control unit according to the present disclosure need not necessarily be provided in the wearable biological information detection device. For example, the control unit according to the present disclosure may be provided in a host device of the system such as a server device. Alternatively, the control unit according to the present disclosure may be provided in an information processing device, such as a smartphone, that is linked with the wearable biological detection device. Further, in the embodiment described above, the BLE standard is exemplified as the communication standard used for the communication between the wearable biological information detection device and the stationary biological information detection device, but the communication standard is not limited to the BLE standard as long as the present disclosure can be implemented.

In the embodiment described above, as the wearable biological information detection device according to the present disclosure, the wearable device, such as the activity tracker and the smart watch worn by the subject on their wrist or the like, is exemplified, but the wearable biological detection device according to the present disclosure includes not only a device worn outside the body of the subject, but also a device embedded inside the body of the subject.

In the embodiment described above, as the data including the second biological information transmitted from the stationary biological information detection device, the advertising packet is exemplified that is one type of the beacon packet receivable by an unspecified large number of devices operating in accordance with the same communication standard, but the data transmitted from the stationary biological information detection device is not limited to the beacon packet such as the advertising packet. As long as the data is embedded with a plurality of pieces of biological information, the present disclosure may be implemented using a communication method other than the beacon using the BLE standard. For example, when the stationary biological information detection device transmits the advertising packet embedded with the plurality of pieces of biological information, the advertising packet may be issued using a broadcast type communication method, or may be issued using a connection type communication method.

In the embodiment described above, the first operation display unit 14, which is the touch panel type display device, is exemplified as the first notification unit for notifying that the wearable biological information detection device is removable, and also that the communication with the stationary biological information detection device has been cut off, but the first notification unit according to the present disclosure is not limited to the touch panel type display device. For example, a speaker may be used as the first notification unit to notify the information described above using an audio output from the speaker. Alternatively, a vibrator may be used as the first notification unit to notify the information described above using vibrations generated by the vibrator. Alternatively, at least two or more of the display device, the speaker, and the vibrator may be combined to notify the information described above.

In the embodiment described above, an example is illustrated in which at least one of the correlation coefficient and the average of difference absolute values is calculated as the correlation value, but another value may be calculated as the correlation value as long as the value indicates a correlation between the first vital signs data and the second vital signs data. Further, in the embodiment described above, an example is illustrated in which the predetermined correlation condition includes at least one of the first correlation condition that is, among the correlation coefficients calculated respectively for the plurality of subjects, a correlation coefficient greater than the first threshold value, the second correlation condition that is, among the averages of difference absolute values calculated respectively for the plurality of subjects, an average of difference absolute values smaller than the second threshold value, the third correlation condition that is a largest correlation coefficient among the correlation coefficients calculated respectively for the plurality of subjects, and the fourth correlation condition that the average of difference absolute values is smallest among the averages of difference absolute values calculated respectively for the plurality of subjects. If the advertising packet only includes the second vital signs data of one of the subjects, the predetermined correlation condition may include at least one of the first correlation condition that the correlation coefficient is greater than the first threshold value, and the second correlation condition that the average of difference absolute values is smaller than the second threshold value.

A biological information detection system according to an aspect of the present disclosure may have the following configuration.

A biological information detection system according to an aspect of the present disclosure includes a wearable biological information detection device, a stationary biological information detection device, and a control unit. The wearable biological information detection device includes a first detection unit configured to detect first biological information, the first biological information being biological information of a wearer, and a first communication unit configured to communicate with the stationary biological information detection device. The stationary biological information detection device includes a second detection unit configured to detect second biological information, the second biological information being biological information of a subject, and a second communication unit configured to transmit data including the second biological information. When the data is received by the first communication unit, the control unit calculates a correlation value between the first biological information detected by the first detection unit and the second biological information included in the data, and, when the calculated correlation value satisfies a predetermined correlation condition, causes the wearable biological information detection device to start monitoring the second biological information included in the data, as the biological information of the wearer.

In the biological information detection system according to the aspect of the present disclosure, the correlation value may include at least one of a correlation coefficient and an average of difference absolute values, and the correlation condition may include at least one of a first correlation condition that the correlation coefficient is greater than a first threshold value, and a second correlation condition that the average of difference absolute values is smaller than a second threshold value.

In the biological information detection system according to the aspect of the present disclosure, when the second biological information of a plurality of the subjects is included in the data, the control unit may calculate the correlation value between the first biological information and the second biological information for each of the plurality of subjects, and may cause the wearable biological information detection device to start monitoring the second biological information with which a correlation value that satisfies the correlation condition, among the calculated correlation values, is obtained.

In the biological information detection system according to the aspect of the present disclosure, the correlation value may include at least one of a correlation coefficient and an average of difference absolute values, and the correlation condition may include at least one of a first correlation condition that is, among the correlation coefficients calculated respectively for the plurality of subjects, a correlation coefficient greater than a first threshold value, a second correlation condition that is, among the averages of difference absolute values calculated respectively for the plurality of subjects, an average of difference absolute values smaller than a second threshold value, a third correlation condition that is a largest correlation coefficient among the correlation coefficients calculated respectively for the plurality of subjects, and a fourth correlation condition is a smallest average of difference absolute value among the averages of difference absolute values calculated respectively for the plurality of subjects.

In the biological information detection system according to the aspect of the present disclosure, the wearable biological information detection device may further include a first storage unit configured to store the second biological information included in the data received by the first communication unit, after the monitoring is started, and a first notification unit configured to notify that the wearable biological information detection device is removable, after the monitoring is started, and the first detection unit may stop detecting the first biological information after the monitoring is started.

In the biological information detection system according to the aspect of the present disclosure, when the data is not received by the first communication unit after the monitoring is started, the first notification unit may notify that communication with the stationary biological information detection device is cut off, and the first detection unit may restart detecting the first biological information.

In the biological information detection system according to the aspect of the present disclosure, the second communication unit may transmit a beacon packet including the second biological information, as the data including the second biological information.

A wearable biological information detection device according to an aspect of the present disclosure may have the following configuration.

A wearable biological information detection device according to an aspect of the present disclosure includes a first detection unit configured to detect first biological information, the first biological information being biological information of a wearer, a first communication unit configured to communicate with a stationary biological information detection device configured to detect second biological information, the second biological information being biological information of a subject, and a control unit configured, when data from the stationary biological information detection device is received by the first communication unit, to calculate a correlation value between the first biological information detected by the first detection unit and the second biological information included in the data, and, when the calculated correlation value satisfies a predetermined correlation condition, to cause the wearable biological information detection device to start monitoring the second biological information included in the data as the biological information of the wearer.

In the wearable biological information detection device according to the aspect of the present disclosure, the correlation value may include at least one of a correlation coefficient and an average of difference absolute values, and the correlation condition may include at least one of a first correlation condition that the correlation coefficient is greater than a first threshold value, and a second correlation condition that the average of difference absolute values is smaller than a second threshold value.

In the wearable biological information detection device according to the aspect of the present disclosure, when the second biological information of a plurality of the subjects is included in the data, the control unit may calculate the correlation value between the first biological information and the second biological information for each of the plurality of subjects, and may cause the wearable biological information detection device to start monitoring the second biological information with which a correlation value that satisfies the correlation condition, among the calculated correlation values, is obtained.

In the wearable biological information detection device according to the aspect of the present disclosure, the correlation value may include at least one of a correlation coefficient and an average of difference absolute values, and the correlation condition may include at least one of a first correlation condition that is, among the correlation coefficients calculated respectively for the plurality of subjects, a correlation coefficient greater than a first threshold value, a second correlation condition that is, among the averages of difference absolute values calculated respectively for the plurality of subjects, an average of difference absolute values smaller than a second threshold value, a third correlation condition that is a largest correlation coefficient among the correlation coefficients calculated respectively for the plurality of subjects, and a fourth correlation condition is a smallest average of difference absolute value among the averages of difference absolute values calculated respectively for the plurality of subjects.

The wearable biological information detection device according to the aspect of the present disclosure may further include a first storage unit configured to store the second biological information included in the data received by the first communication unit, after the monitoring is started, and a first notification unit configured to notify that the wearable biological information detection device is removable, after the monitoring is started, and the first detection unit may stop detecting the first biological information after the monitoring is started.

In the wearable biological information detection device according to the aspect of the present disclosure, when the data is not received by the first communication unit after the monitoring is started, the first notification unit may notify that communication with the stationary biological information detection device is cut off, and the first detection unit may restart detecting the first biological information.

In the wearable biological information detection device according to the aspect of the present disclosure, the data received from the stationary biological information detection device by the first communication unit may be a beacon packet including the second biological information.

A biological information detection method according to an aspect of the present disclosure may have the following configuration.

A biological information detection method according to an aspect of the present disclosure uses a wearable biological information detection device configured to detect biological information of a wearer as first biological information, and a stationary biological information detection device configured to detect biological information of a subject as second biological information. The method includes, when data from the stationary biological information detection device is received by the wearable biological information detection device, calculating a correlation value between the first biological information detected by the wearable biological information detection device, and the second biological information included in the data, and, when the calculated correlation value satisfies a predetermined correlation condition, causing the wearable biological information detection device to start monitoring the second biological information included in the data, as the biological information of the wearer.

What is claimed is:
1. A wearable biological information detection device comprising:

a first sensor configured to detect first biological information, the first biological information being biological information of a wearer;
a first transceiver configured to communicate with a stationary biological information detection device configured to detect second biological information, the second biological information being biological information of a subject; and
a control unit configured, when data from the stationary biological information detection device is received in a format of data packet by the first transceiver, to calculate a correlation value between the first biological information detected by the first sensor and the second biological information included in the data, and when the calculated correlation value satisfies a predetermined correlation condition, to automatically associate and cause the wearable biological information detection device to start monitoring the second biological information included in the data as the biological information of the wearer, and to deactivate the first sensor for detecting the first biological information after the second biological information included in the data transmitted from the stationary biological information detection device is associated and monitored as the biological information of the wearer.

2. The wearable biological information detection device according to claim 1, wherein
the correlation value includes at least one of a correlation coefficient and an average of difference absolute values, and
the correlation condition includes at least one of a first correlation condition that the correlation coefficient is greater than a first threshold value, and a second correlation condition that the average of difference absolute values is smaller than a second threshold value.

3. The wearable biological information detection device according to claim 1, wherein
when the second biological information of a plurality of the subjects is included in the data, the control unit calculates the correlation value between the first biological information and the second biological information for each of the plurality of subjects, and causes the wearable biological information detection device to start monitoring the second biological information with which a correlation value that satisfies the correlation condition, among the calculated correlation values, is obtained.

4. The wearable biological information detection device according to claim 3, wherein
the correlation value includes at least one of a correlation coefficient and an average of difference absolute values, and
the correlation condition includes at least one of a first correlation condition that is, among the correlation coefficients calculated respectively for the plurality of subjects, a correlation coefficient greater than a first threshold value, a second correlation condition that is, among the averages of difference absolute values calculated respectively for the plurality of subjects, an average of difference absolute values smaller than a second threshold value, a third correlation condition that is a largest correlation coefficient among the correlation coefficients calculated respectively for the plurality of subjects, and a fourth correlation condition is a smallest average of difference absolute value among the averages of difference absolute values calculated respectively for the plurality of subjects.

5. The wearable biological information detection device according to claim 1, further comprising:
a first memory configured to store the second biological information included in the data received by the first transceiver, after the monitoring is started, and
a first notification unit configured to notify that the wearable biological information detection device is removable, after the monitoring is started.

6. The wearable biological information detection device according to claim 5, wherein
when the data is not received by the first transceiver after the monitoring is started,
the first notification unit notifies that communication with the stationary biological information detection device is cut off, and
the first sensor restarts detecting the first biological information.

7. The wearable biological information detection device according to claim 1, wherein
the data received from the stationary biological information detection device by the first transceiver is a beacon packet including the second biological information.

8. A biological information detection system comprising:
a wearable biological information detection device; and
a stationary biological information detection device;
wherein
the wearable biological information detection device includes:
a control unit;
a first sensor configured to detect first biological information, the first biological information being biological information of a wearer; and
a first transceiver configured to communicate with the stationary biological information detection device,
the stationary biological information detection device includes:
a second sensor configured to detect second biological information, the second biological information being biological information of a subject; and
a second transceiver configured to transmit data including the second biological information in a format of data packet, and
when the data is received by the first transceiver and the control unit, the control unit calculates a correlation value between the first biological information detected by the first sensor and the second biological information included in the data, and wherein when the calculated correlation value satisfies a predetermined correlation condition, the control unit automatically associates and causes the wearable biological information detection device to start monitoring the second biological information included in the data, as the biological information of the wearer, and the control unit deactivates the first sensor for detecting the first biological information after the second biological information included in the data transmitted from the stationary biological information detection device is associated and monitored as the biological information of the wearer.

9. The biological information detection system according to claim 8, wherein
the correlation value includes at least one of a correlation coefficient and an average of difference absolute values, and the correlation condition includes at least one of a first correlation condition that the correlation coefficient is greater than a first threshold value, and a second correlation condition that the average of difference absolute values is smaller than a second threshold value.

10. The biological information detection system according to claim 8, wherein
when the second biological information of a plurality of the subjects is included in the data, the control unit calculates the correlation value between the first biological information and the second biological information for each of the plurality of subjects, and causes the wearable biological information detection device to start monitoring the second biological information with which a correlation value that satisfies the correlation condition, among the calculated correlation values, is obtained.

11. The biological information detection system according to claim 10, wherein
the correlation value includes at least one of a correlation coefficient and an average of difference absolute values, and
the correlation condition includes at least one of a first correlation condition that is, among the correlation coefficients calculated respectively for the plurality of subjects, a correlation coefficient greater than a first threshold value, a second correlation condition that is, among the averages of difference absolute values calculated respectively for the plurality of subjects, an average of difference absolute values smaller than a second threshold value, a third correlation condition that is a largest correlation coefficient among the correlation coefficients calculated respectively for the plurality of subjects, and a fourth correlation condition is a smallest average of difference absolute value among the averages of difference absolute values calculated respectively for the plurality of subjects.

12. The biological information detection system according to claim 8, wherein
the wearable biological information detection device further includes
a first memory configured to store the second biological information included in the data received by the first transceiver, after the monitoring is started, and
a first notification unit including at least one of display, speaker, and vibrator configured to notify that the wearable biological information detection device is removable, after the monitoring is started.

13. The biological information detection system according to claim 12, wherein
when the data is not received by the first transceiver after the monitoring is started,
the first notification unit notifies that communication with the stationary biological information detection device is cut off, and
the first sensor restarts detecting the first biological information.

14. The biological information detection system according to claim 8, wherein
the second transceiver transmits a beacon packet including the second biological information, as the data including the second biological information.

15. A biological information detection method using a wearable biological information detection device configured to detect biological information of a wearer as first biological information, and a stationary biological information detection device configured to detect biological information of a subject as second biological information, the method comprising:
when data from the stationary biological information detection device is received in a format of data packet by the wearable biological information detection device, calculating a correlation value between the first biological information detected by the wearable biological information detection device, and the second biological information included in the data; and
when the calculated correlation value satisfies a predetermined correlation condition, automatically associating and causing the wearable biological information detection device to start monitoring the second biological information included in the data, as the biological information of the wearer, and deactivating the first sensor for detecting the first biological information after the second biological information included in the data transmitted from the stationary biological information detection device is associated and monitored as the biological information of the wearer.

* * * * *